(12) United States Patent
Wijesekera

(10) Patent No.: US 7,034,192 B2
(45) Date of Patent: Apr. 25, 2006

(54) METHOD FOR REMOVAL OF ACETOL FROM PHENOL

(75) Inventor: Tilak P. Wijesekera, Boothwyn, PA (US)

(73) Assignee: Sunoco Inc. (R&M), Philadelphia, PA (US)

( * ) Notice: Subject to any disclaimer, the term of this patent is extended or adjusted under 35 U.S.C. 154(b) by 0 days.

(21) Appl. No.: 10/915,723

(22) Filed: Aug. 9, 2004

(65) Prior Publication Data

US 2005/0215834 A1 Sep. 29, 2005

Related U.S. Application Data

(60) Provisional application No. 60/556,236, filed on Mar. 24, 2004.

(51) Int. Cl.
*C07C 37/86* (2006.01)
*C07C 37/74* (2006.01)
*C07C 37/70* (2006.01)
*C07C 37/68* (2006.01)

(52) U.S. Cl. .................. 568/754; 568/757; 568/749

(58) Field of Classification Search ................ 568/754, 568/757, 749
See application file for complete search history.

(56) References Cited

U.S. PATENT DOCUMENTS

| | | | |
|---|---|---|---|
| 2,910,511 A | 10/1959 | Joris | |
| 2,971,893 A | 2/1961 | Hood | |
| 2,992,169 A | 7/1961 | Gregory et al. | |
| 3,087,969 A | 4/1963 | Widiger | |
| 3,335,070 A | 8/1967 | Adams | |
| 3,454,653 A | 7/1969 | Larson | |
| 3,810,946 A | 5/1974 | Yeh et al. | |
| 4,298,765 A | 11/1981 | Cochran et al. | |
| 4,857,151 A | 8/1989 | Suciu et al. | |
| 5,414,154 A | 5/1995 | Jenczewski et al. | |
| 6,066,767 A | 5/2000 | Zakoshansky et al. | |
| 6,346,645 B1 | 2/2002 | Kulprathipanja et al. | |
| 6,486,365 B1 | 11/2002 | Fulmer et al. | |
| 6,489,519 B1 | 12/2002 | van Barneveld et al. | |
| 6,573,408 B1 | 6/2003 | Fulmer et al. | |
| 6,576,798 B1 | 6/2003 | Aristovich et al. | |
| 6,635,789 B1 | 10/2003 | Fulmer et al. | |
| 2004/0158105 A1 | 8/2004 | Payne | 568/810 |
| 2004/0158106 A1 | 8/2004 | Payne | 568/810 |

FOREIGN PATENT DOCUMENTS

| | | |
|---|---|---|
| EP | 0004168 B1 | 1/1984 |
| EP | 0190790 B1 | 7/1989 |
| EP | 0568817 B1 | 3/1997 |
| GB | 865677 | 4/1961 |
| GB | 920905 | 3/1965 |
| GB | 1108327 | 4/1968 |
| GB | 1171854 | 11/1969 |

*Primary Examiner*—Elvis O. Price
(74) *Attorney, Agent, or Firm*—Robert A. Koons, Jr.; Matthew P. McWilliams; Drinker Biddle & Reath LLP

(57) ABSTRACT

A method is provided for the efficient, low cost removal of acetol from a phenol stream. The method results in removal of substantially all of the acetol from the phenol stream without the formation of substantial amounts of additional methylbenzofuran. The method also avoids the use of expensive reagents and capital intensive distillation equipment.

4 Claims, 4 Drawing Sheets

METHOD FOR REMOVAL OF ACETOL FROM PHENOL

REFERENCE TO RELATED APPLICATIONS

This application claims priority under 35. U.S.C. § 119(e) to Provisional Patent Application Ser. No. 60/556,236, which was filed on Mar. 24, 2004.

FIELD OF THE INVENTION

The present invention relates to the field of the production of high purity phenol. More particularly, the present invention relates to the removal of acetol from phenol to obtain desired high purity.

BACKGROUND OF THE INVENTION

The process commonly practiced for the production of phenol involves the oxidation of cumene to cumene hydroperoxide, followed by its acid catalyzed decomposition to phenol and acetone. Isolation of phenol from the reaction product involves the neutralization of the acid catalyst followed by a series of distillation and separation steps. The lower boiling components such as acetone, unreacted cumene as well as α-methylstyrene (AMS) are first recovered from the crude product by distillation. The remaining material is introduced into a phenol recovery column in which phenol is distilled away from the higher boiling impurities. Depending on the distillation procedures used to recover acetone, cumene and AMS, the distilled phenol may contain minor quantities of impurities such as mesityl oxide (MO), acetol (hydroxyacetone) and other aliphatic carbonyl compounds, olefinic compounds, acetophenone, cumylphenols and 2- and 3-methylbenzofuran (MBF) in addition to residual amounts of acetone, cumene and AMS. Such impurities are undesirable in phenol used in certain applications such as in the manufacture of bisphenol-A.

MBF is a particularly undesirable contaminant of phenol that is used for certain applications such as in the production of bisphenol-A, a precursor to polycarbonate resins. Due to similar volatility, MBF cannot be separated from phenol by fractional distillation. U.S. Pat. Nos. 5,064,507 and 4,857,151 describe a process of distillation in the presence of water (also called steam stripping) to reduce MBF in phenol. However, due to the high energy costs and the necessity to use large distillation columns, this process is expensive in terms of capital investment and operating costs. U.S. Pat. No. 5,414,154 describes the use of a strong acid ion exchange resin to reduce the level of MBF by converting it to higher boiling compounds. U.S. Pat. No. 5,414,154 also showed that the effectiveness of MBF removal by resin treatment increases with an increase in temperature.

Although strong acid ion exchange resins also remove carbonyl compounds from phenol on contact, acetol reacts with phenol to produce more MBF. U.S. Pat. No. 5,414,154 teaches the necessity to remove acetol from phenol (e.g. by treatment with an amine) prior to contact with the resin to remove MBF.

Although effective, amine treatment involves the use of an expensive reagent, which must subsequently be purged from the phenol stream.

Both U.S. Pat. Nos. 3,810,946 and 6,489,519 disclose treatment of a phenol stream containing acetol with an acid or acid resin to remove acetol. British Patent 0 865 677 discloses a process for removing acetol from a phenol stream wherein the phenol stream is heated in the presence or absence of a catalyst. However, in all of these patents, acetol is removed by reacting it with phenol to form MBF, which is subsequently purged from the phenol stream.

European Patent 0 004 168 and U.S. Pat. No. 4,857,151 disclose distillation processes to remove acetol from phenol streams. However, these methods involve the use of capital intensive distillation apparatus.

There remains a need for an efficient, low cost method for the removal of acetol from a phenol stream that does not adversely affect phenol yields by formation of a significant amount of additional MBF.

SUMMARY OF THE INVENTION

The present invention provides efficient, low cost methodologies for the removal of acetol from a phenol stream.

In one embodiment of the present invention, a method for the efficient, low cost removal of acetol from phenol comprises contacting a phenol stream containing acetol with an acidic resin at a temperature of about 85° C. or less to convert acetol into higher boiling compounds other than methylbenzofuran. The phenol stream is then distilled to separate phenol from the higher boiling compounds.

In another embodiment of the present invention, a method for the efficient, low cost removal of acetol from phenol comprises adding an alkali metal hydroxide to the phenol stream to obtain an alkali metal hydroxide concentration of 600 ppm by weight or less based on phenol. The phenol stream is then heated at a temperature of greater than about 175° C. to convert acetol into higher boiling compounds other than methylbenzofuran. The phenol stream is then distilled to separate phenol from the higher boiling compounds.

In both embodiments of the present invention, acetol is effectively removed without reacting a large portion of the acetol with phenol, thus the present method results in reduced MBF formation and improved phenol yields.

DESCRIPTION OF THE INVENTION

It has been discovered that acetol can be removed efficiently from phenol at a low cost while minimizing the formation of methylbenzofuran (MBF). The treatment to remove acetol involves a treatment of distilled phenol containing acetol with either an acidic resin at low temperature or a small amount of caustic at elevated temperature. By this treatment, acetol present in the crude phenol is converted primarily to high boiling products other than MBF. These high boiling products can then be separated from phenol via distillation.

The removal of acetol is key to the subsequent efficient removal of MBF from the crude phenol. As is known, at the high temperatures and acidic conditions used to convert MBF to products separable from phenol, acetol reacts with phenol to produce more MBF. This reaction has the dual effect of reducing phenol recovery and making the removal of MBF from the product less efficient.

In one embodiment of the invention, a distilled phenol stream containing acetol is contacted with an acidic resin at a temperature of about 85° C. or less to convert acetol to higher boiling compounds other than MBF. Following the acidic resin treatment, phenol is separated from the higher boiling compounds by distillation. Treatment time and temperature will vary based on the quantity of acetol to be removed from the crude phenol. Treatment times can vary from 5 minutes to 1 hour. In an exemplary treatment 700 ppm of acetol was removed from a crude phenol stream by contacting with an acidic resin at a temperature of about 85° C. for about 15 minutes. Only about 12% of the acetol in this example was converted into MBF.

It is preferred that the acidic resin be in the form of a fixed bed, over which the phenol stream is passed. The phenol stream is preferably passed over the resin bed at a rate of from 1 to 12 bed volumes per hour.

Figure 1:
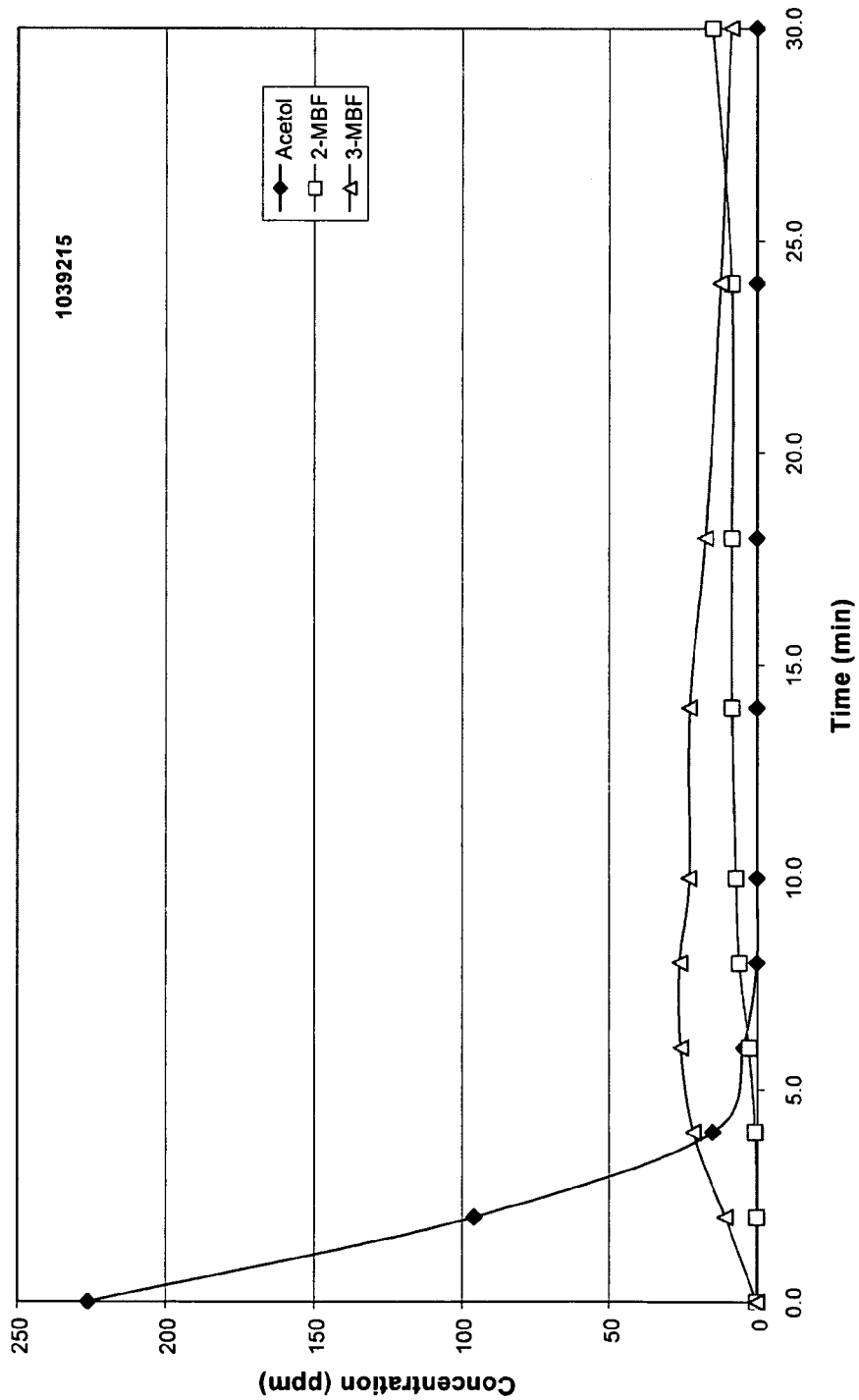
FIG. 1—Illustrates the removal of acetol from a phenol stream by reaction with an acidic resin at 83° C.
Figure 2:
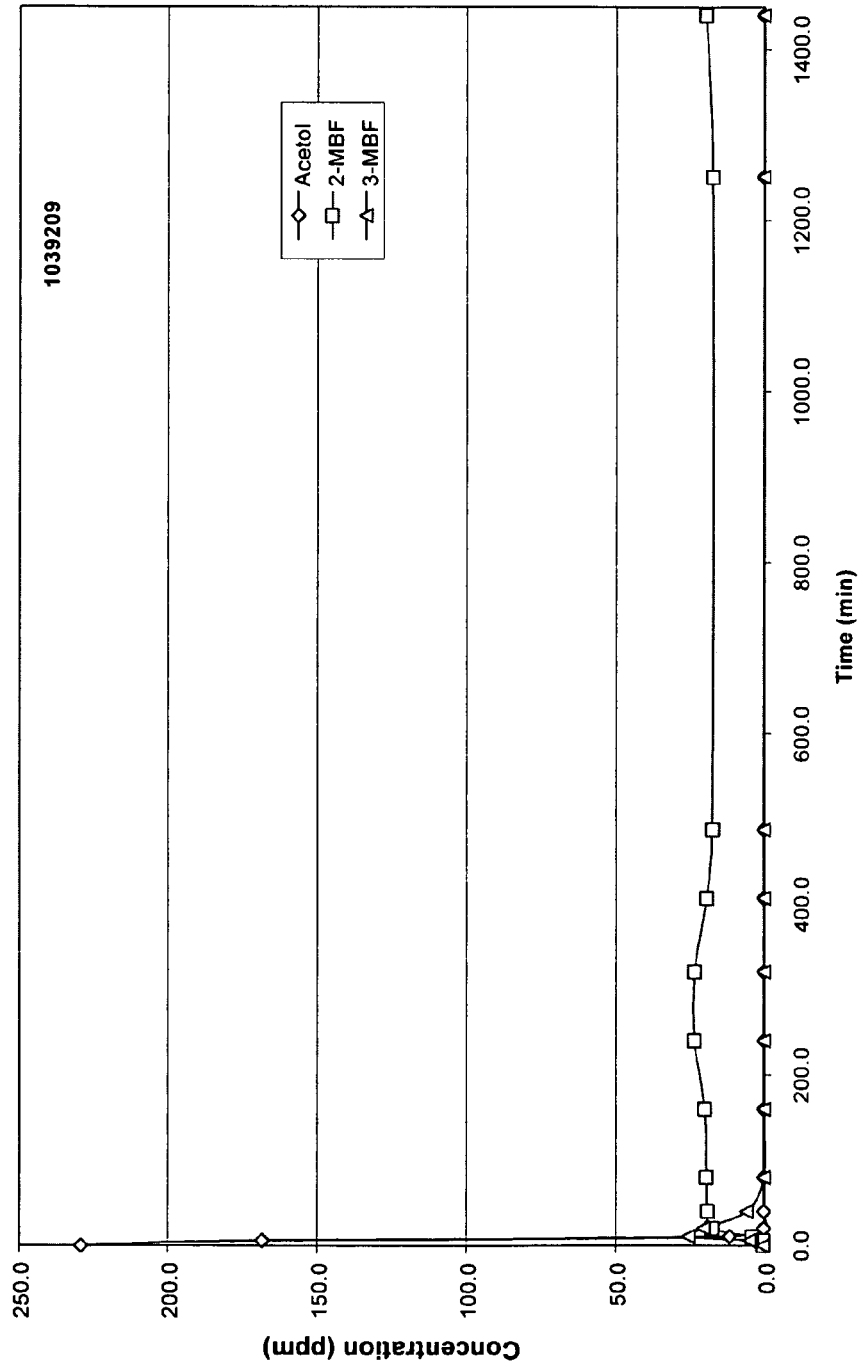
FIG. 2—Illustrates the removal of acetol from a phenol stream by reaction with an acidic resin at 85° C. and the absence of the formation of significant amounts of MBF on standing at 85° C.

FIG. 1 shows the rapid reduction of acetol in a sample of phenol from about 225 ppm by weight to near 0 ppm on treatment with Amberlyst 36 at 83° C. Note that the formation of MBF is minimal. If all of the acetol were to be converted to MBF, a total concentration of about 400 ppm by weight of MBF would be expected. Instead, the combined concentration of 2-MBF and 3-MBF is only about 25 ppm by weight. FIG. 2 again shows the treatment of a crude phenol stream containing about 225 ppm by weight of acetol at 85° C. with Amberlyst 36. Again, the reduction in acetol content to near 0 ppm is extremely rapid, with a minimal formation of MBF. As can further be seen in FIG. 2, the extended hold time at 85° C. does not result in an increase in the content of MBF. This indicates that the heavy products produced from acetol by the acid resin treatment are stable at that temperature.

The distillation following the acid resin treatment is preferably a flash distillation performed at reduced pressure to avoid the formation of MBF that would result from the breakdown of high molecular weight species formed during the acid treatment. The use of a flash distillation under vacuum has the added advantage of eliminating costly distillation apparatus used to separate phenol and acetol in prior art methods. It will be recognized however, that various distillation methods can be used in conjunction with the invention as long as care is taken to avoid decomposition of the high molecular weight species formed during the acid treatment.

Figure 3:
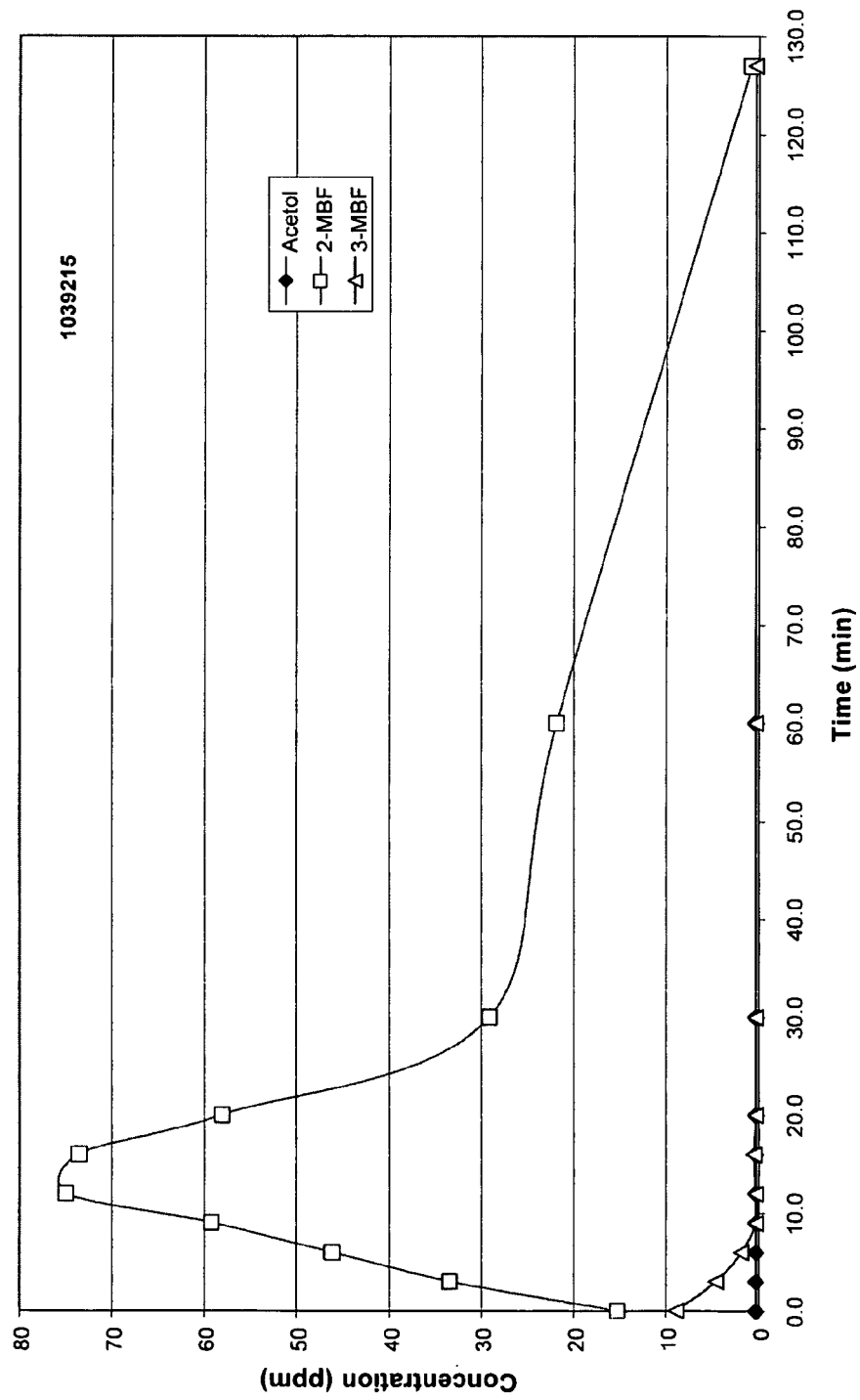
FIG. 3—Illustrates the formation of MBF that occurs when a phenol stream treated with acidic resin at 85° C. is contacted directly with an acidic resin at 133° C.

Referring to FIG. 3, the necessity of avoiding the decomposition of the heavy products formed during the acid resin treatment is illustrated. FIG. 3 shows the effect of a high temperature resin treatment on a phenol stream that has been treated by acidic resin at 85° C. to convert acetol to higher boiling compounds, without first removing the higher boiling products. As can be seen, the elevated temperature resulted in the formation of additional MBF. This indicates that the higher boiling compounds formed in the low temperature acidic resin treatment are decomposing back to acetol at high temperature in the presence of the acidic resin, and then reacting with phenol to form MBF. Not only does this result in a loss of phenol, but as can be seen, the time necessary to reduce the MBF content to near 0 ppm by weight is extended significantly, approximately 130 minutes.

Figure 4:
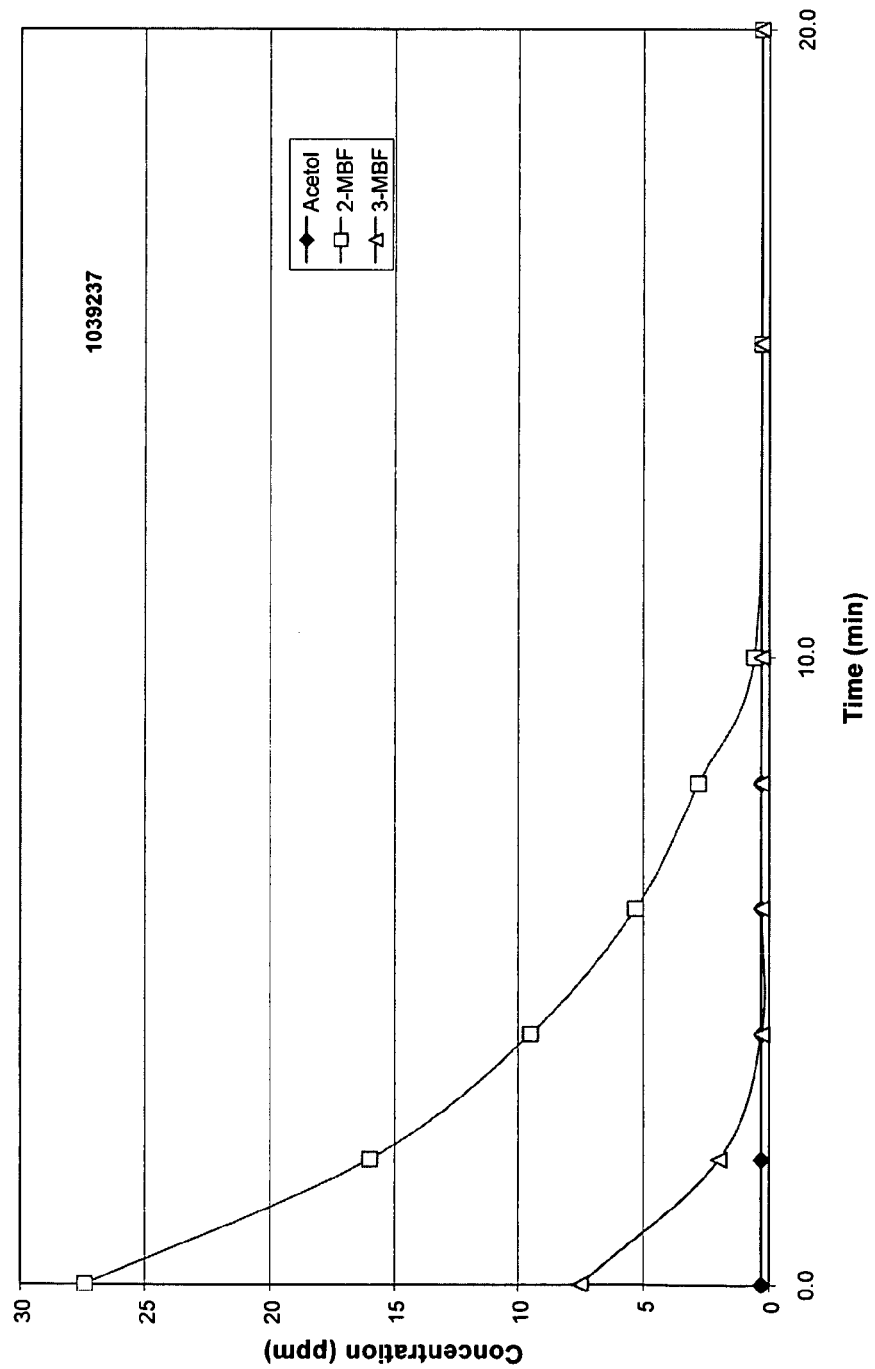
FIG. 4—Illustrates the efficient removal of MBF from a phenol stream by reaction with an acidic resin at 134° C. after high boiling materials formed from acetol have been removed by a low temperature treatment with acid resin.

FIG. 4 illustrates an example where the higher boiling compounds formed by treatment with acidic resin are removed by flash distillation of the phenol prior to acidic resin treatment at elevated temperature to remove MBF. As can be seen in FIG. 4, no increase in MBF content is experienced. Further, the MBF content is reduced to near 0 ppm in about 10 minutes, as opposed to 130 minutes.

In an alternative embodiment of the invention, a distilled phenol stream containing acetol is treated with a small amount of caustic at elevated temperature to convert acetol to higher boiling compounds other than MBF. Again, the phenol is separated from the higher boiling compounds via distillation. The temperatures used for the caustic treatment will be at least 175 to 225° C. The caustic is preferably added as a concentrated solution, e.g. 50 percent by weight. The treatment time and temperature required for the removal of acetol in this embodiment will vary based on the amount of acetol to be removed and the quantity of caustic used. In an exemplary treatment 1800 ppm of acetol was reduced to less than 10 ppm by treatment with 130 ppm of caustic at 200° C. for 4.5 hours. In this example only 3 percent of the acetol was converted into MBF. It should be pointed out that the use of caustic at elevated temperatures requires a low water content in the phenol stream being treated. Various methods for reducing the water content of organic streams, and phenol in particular, are known in the art. Other examples reducing acetol from 1800 and 1045 ppm are shown in Table 1 below.

TABLE 1

Acetol Removal By Heat Treatment With Added Caustic

| Temperature | 50% Caustic Concentration | | |
|---|---|---|---|
| | 260 ppm | 525 ppm | 1100 ppm |
| 1800 ppm Acetol to 10 ppm | | | |
| 175° C. | >7 hr | | |
| 190° C. | 5 hr | 5 hr | |
| 198° C. | 4.5 hr | 3.5 hr | 2.3 hr* |
| 1045 ppm Acetol to 10 ppm | | | |
| 198° C. | 2 hr | | |

*2.75 hr at 1.5% water concentration

Following the treatment to remove acetol, the phenol is distilled from the higher boiling compounds, and can be passed to an acidic resin treatment at elevated temperature to remove MBF, as disclosed in U.S. Pat. Nos. 5,414,154 and 6,388,144B1, both of which are incorporated herein by reference in their entirety.

The present method to remove acetol from phenol has the advantage of being more cost efficient than prior art methods that involved the use of distillation apparatus, such as super splitter columns and prior art methods that used expensive amines. In addition, the present method has the advantage of producing less MBF than other prior art methods, which utilized high concentrations of caustic or relied on multiple high temperature treatments with acidic resins.

What is claimed is:

1. A method for removing acetol and methylbenzofuran from a phenol stream, said method comprising:

contacting a phenol stream containing acetol and methylbenzofuran with a first acidic resin at a temperature of about 85°C or less, to convert acetol into higher boiling compounds other than methylbenzofuran, distilling said phenol stream to separate phenol containing methylbenzofuran from said higher boiling compounds, and contacting said phenol containing methylbenzofuran with a second acidic resin at an elevated temperature to convert methylbenzofuran to compounds separable from phenol by distillation.

2. The method of claim 1, wherein said phenol is separated from said higher boiling compounds by a flash distillation.

3. The method according to claim 1, wherein said acidic resin is in a fixed bed.

4. The method according to claim 3, wherein said phenol stream is contacted with said acidic resin at a rate of about 1 to about 12 bed volumes per hour.

* * * * *